(12) United States Patent
Lach et al.

(10) Patent No.: US 11,065,174 B2
(45) Date of Patent: Jul. 20, 2021

(54) WEARABLE INTERACTIVE SYSTEM AND METHOD OF NON-OPIOID AND DRUG-FREE PAIN CONTROL

(71) Applicants: Rebecca Lach, Philadelphia, PA (US); Elliot Lach, Boston, MA (US)

(72) Inventors: Rebecca Lach, Philadelphia, PA (US); Elliot Lach, Boston, MA (US)

(*) Notice: Subject to any disclaimer, the term of this patent is extended or adjusted under 35 U.S.C. 154(b) by 190 days.

(21) Appl. No.: 15/932,332

(22) Filed: Feb. 16, 2018

(65) Prior Publication Data

US 2018/0228689 A1    Aug. 16, 2018

Related U.S. Application Data (60) Provisional application No. 62/459,853, filed on Feb. 16, 2017.

(51) Int. Cl.
*A61H 9/00* (2006.01)
*A61H 39/00* (2006.01)
(Continued)

(52) U.S. Cl.
CPC ......... *A61H 9/0078* (2013.01); *A61H 9/0057* (2013.01); *A61H 9/0071* (2013.01); *A61H 39/007* (2013.01); *A61N 5/0622* (2013.01); *A61H 2201/165* (2013.01); *A61H 2205/02* (2013.01); *A61H 2205/06* (2013.01); *A61H 2205/065* (2013.01); *A61H 2205/10* (2013.01);
(Continued)

(58) Field of Classification Search
CPC .... A61H 9/007; A61H 9/0057; A61H 9/0071; A61H 9/0078; A61H 15/00; A61H 15/0078; A61H 15/02; A61H 23/004; A61H 23/00; A61H 23/006; A61H 23/024; A61H 23/02; A61H 39/007; A61N 5/0622
USPC ....................................................... 601/151
See application file for complete search history.

(56) References Cited

U.S. PATENT DOCUMENTS

| | | | | |
|---|---|---|---|---|
| 5,672,148 A | * | 9/1997 | Maunier | A61H 9/0078 601/148 |
| 6,179,796 B1 | * | 1/2001 | Waldridge | A61H 9/0078 601/149 |

(Continued)

OTHER PUBLICATIONS

Anatomy of the Human Body. Henry Gray. Accessed at https://www.bartleby.com/107/illus606.html (Year: 1918).*
(Continued)

*Primary Examiner* — Valerie L Woodward
*Assistant Examiner* — Paige Kathleen Bugg
(74) *Attorney, Agent, or Firm* — Cozen O'Connor (57) ABSTRACT

A wearable sleeve is configured to be worn on a limb of a user. The sleeve includes a flexible tubular sleeve body that is elongate along an axis. The sleeve further includes at least one of a series of vibrating elements and a series of pneumatic compression elements that are attached to the tubular sleeve body. During use, the vibrating elements and/or the compression elements are configured to be disposed along a lymphatic drainage path of the user. Targeted photonic stimulation in the form of light generated by LED or laser may be employed to further enhance the circulatory and physiologic changes. Microprocessor incorporated control and interactive capability further results in optimized application and patient compliance due to improved efficacy.

16 Claims, 5 Drawing Sheets

(51) Int. Cl.
*A61N 5/06* (2006.01)
*A61N 1/36* (2006.01)
*A61N 5/067* (2006.01)

(52) U.S. Cl.
CPC ...... *A61H 2209/00* (2013.01); *A61N 1/36021* (2013.01); *A61N 5/0613* (2013.01); *A61N 2005/067* (2013.01); *A61N 2005/0645* (2013.01); *A61N 2005/0651* (2013.01)

(56) References Cited

U.S. PATENT DOCUMENTS

| | | | | |
|---|---|---|---|---|
| 6,656,141 | B1* | 12/2003 | Reid | A61B 17/1325 601/134 |
| 7,044,924 | B1* | 5/2006 | Roth | A61H 9/0078 128/DIG. 20 |
| 7,135,007 | B2 | 11/2006 | Scott | A61F 13/085 602/75 |
| 10,271,981 | B2* | 4/2019 | Raniere | A61F 5/012 |
| 2002/0042585 | A1 | 4/2002 | Kloecker | |
| 2008/0004548 | A1* | 1/2008 | Oshmyansky | A61H 9/0078 601/2 |
| 2010/0249637 | A1* | 9/2010 | Walter | A61H 23/02 600/544 |
| 2011/0034253 | A1 | 2/2011 | Roll | |
| 2014/0277298 | A1* | 9/2014 | Tapper | A61N 5/0616 607/91 |
| 2015/0174002 | A1 | 6/2015 | Burbank et al. | |
| 2016/0022536 | A1* | 1/2016 | Nauman | A61H 23/02 601/70 |
| 2016/0030280 | A1 | 2/2016 | Jones et al. | |
| 2016/0331620 | A1* | 11/2016 | Kazanchyan | A61N 1/3603 |
| 2017/0196763 | A1* | 7/2017 | Obma | A61H 9/0092 |

OTHER PUBLICATIONS

Veins of the Upper Extremity Diagram. Accessed at http://www.medicalook.com/human_anatomy/organs/Veins_of_the_Upper_Extremity.html (Year: 2007).*

Rosenberg et al.; "Pressure Sore Prevention System: A new Biofeedback Approach"; Plast Reconstruction Surg; vol. 75; Jun. 1985; p. 926.

"Lymphatic Skin Brushing For Breast And Body Health"; Circuelle Foundation; www.circuellefoundation.org/blog/item/lymphatic-skin-brushing-for-breast-and-body-health.html; Jul. 2015; 8 pages.

International Patent Application No. PCT/US2018/000015; Int'l Search Report and the Written Opinion; dated Aug. 23, 2018; 17 pages.

Julius et al.; "Molecular mechanisms of nociception"; Nature; vol. 413; Sep. 2001; p. 203-210.

Bolay et al.; "Mechanisms of pain modulation in chronic syndromes"; Neurology; vol. 59 (5 suppl 2); Sep. 2002; p. S2-S7.

Dickenson A. H.; "Editorial I: Gate Control Theory of pain stands the test of time"; British Journal of Anaesthesia; vol. 88 Issue 6; Jun. 2002; p. 755-757.

Campbell et al., "Gate Control Theory of Pain"; Encyclopedia of Behavioral Medicine; 2013; p. 832-834.

Almeida et al.; "Afferent pain pathways: a neuroanatomical review"; Brain Research; vol. 1000 Issue1-2; Mar. 2004; p. 40-56.

Oakley et al.; "Spinal Cord Stimulation: Mechanisms of Action"; Spine; vol. 27 Issue 22; Nov. 2002; p. 2574-2583.

Moayedi et al.; "Theories of pain: from specificity to gate control"; Journal of Neurophysiology; vol. 109 Issue 1; Jan. 2013; p. 5-12.

"How Does A Tens Unit Work?"; https://www.tensunits.com/WORK.html; TENSUNITS; © 2018; accessed Oct. 3, 2018; 9 pages.

Karlsson et al.; "Lymphoedema and health-related quality of life by early treatment in long-term survivors of breast cancer. A comparative retrospective study up to 15 years after diagnosis" Supportive Care Cancer; vol. 23 Issue 10; Oct. 2015; p. 2965-2972.

DiSipio et al.; "Incidence of unilateral arm lymphedema after breast cancer: a systematic review and meta-analysis"; The Lancet Oncology; vol. 14 Issue 6; May 2013; p. 500-515.

"Clinical features and diagnosis of peripheral lymphedema"; https://www.uptodate.com/contents/clinical-features-and-diagnosis-of-peripheral-lymphedema; UpToDate Inc.; © 2018; accessed Oct. 3, 2018; 9 pages.

Martin et al.; "Manual lymphatic drainage therapy in patients with breast cancer related lymphoedema"; BMC Cancer; vol. 11:94; 2011; 6 pages.

* cited by examiner

WEARABLE INTERACTIVE SYSTEM AND METHOD OF NON-OPIOID AND DRUG-FREE PAIN CONTROL

CROSS REFERENCE TO RELATED APPLICATIONS

This application claims benefit to U.S. Provisional Application Ser. No. 62/459,853 filed Feb. 16, 2017, the disclosure of which is hereby incorporated by reference in its entirety.

TECHNICAL FIELD

This disclosure relates generally to a wearable sleeve, and specifically to a sleeve that is configured to reduce pain perception and relieve lymphatic obstruction.

BACKGROUND

The use of opiates to control pain can have side effects that include respiratory depression, nausea, reduced gastrointestinal motility, changes in cognitive function, potential for drug addiction and physiological dependence as well as potential for diversion. Non-opiate pharmaceuticals such as nonsteroidal anti-inflammatory drugs (NSAIDS) are also not without risk and are commonly associated with gastric upset, potential for increased bleeding via hematologic alterations in platelet function, cardiovascular risks, tendon rupture, and possible incompatibility with other prescribed or over the counter medications.

SUMMARY

The present application describes a wearable sleeve or garment configured for pain management as well as pain prevention, that utilizes non-pharmaceutical approaches. These approaches capitalize upon the gate control theory of pain and may also address alleviation of other symptoms such as nausea, headache, mental depression, insomnia, snoring, and pressure sores. The gate control theory of pain asserts that sensation of non-painful stimuli closes the "gates" to sensing painful stimuli, which mitigates pain sensation from traveling to the central nervous system. In this way, stimulation via non-noxious input may be used to suppress or minimize the perception of pain. Administration of a non-painful stimulus also results in a distraction phenomenon that may be used to override perceived pain. Administration of a distraction element may also alter conscious behavior to, for example, change body position.

Pain is aggravated by the presence of numerous conditions that may, for example, result in nerve compression, ischemia, or both, conditions that may be associated with compartment syndrome within a confined subfascial space. Pain can also be associated with local cellular histamine or inflammatory cytokine release as well as numerous other mechanisms. Edema, the presence of hematoma, blood breakdown products, and presence of lymphatic flow dysfunction or obstruction with or without infection may also result in pain in conjunction with the associated comorbidities.

In one aspect, the present application describes a wearable sleeve configured to be worn on a limb of a user. The sleeve includes a flexible tubular sleeve body that is elongate along an axis. The sleeve also includes a series of vibrating elements attached to the tubular sleeve body. During use, the vibrating elements are configured to be disposed along a lymphatic drainage path of the user.

In another aspect, a wearable sleeve is configured to be worn on a limb of a user. The sleeve includes a flexible tubular sleeve body that is elongate along an axis. The sleeve also includes a series of pneumatic compression elements attached to the tubular sleeve body. During use, the pneumatic compression elements are configured to sequentially compress along a lymphatic drainage path of the user.

In yet another aspect, a method of alleviating perceived pain of a user employs a wearable sleeve disposed on a limb of the user. The method includes at least one of an activating step and a compressing step. The activating step including a step of activating a series of vibrating elements attached to a tubular sleeve body, the vibrating elements being disposed along a lymphatic drainage path of the user. The compressing step including a step of sequentially compressing a series of pneumatic compression elements attached to the tubular sleeve body so as to sequentially compress along a lymphatic drainage path of the user.

BRIEF DESCRIPTION OF THE DRAWINGS

The foregoing summary, as well as the following detailed description of illustrative embodiments of the wearable sleeve of the present application, will be better understood when read in conjunction with the appended drawings. For the purposes of illustrating the wearable sleeve of the present application, there is shown in the drawings illustrative embodiments. It should be understood, however, that the application is not limited to the precise arrangements and instrumentalities shown. In the drawings.

DETAILED DESCRIPTION OF THE ILLUSTRATIVE EMBODIMENTS

Aspects of the disclosure will now be described in detail with reference to the drawings, wherein like reference numbers refer to like elements throughout, unless specified otherwise. Certain terminology is used in the following description for convenience only and is not limiting.

Nociception is a bioelectrical process whereby changes in response to mechanical, chemical, or thermal stimuli lead to the cognitive and emotional experience of pain. A-delta fibers are localized, sharp, thinly myelinated fibers that modulate the first pain signal perceived by the body upon acute injury. These primary sensory fibers originate in the dorsal root of the spinal cord and project to ascending brain centers including the reticular formation, thalamus, and cerebral cortex whereby the conscious perception of pain is conveyed.

Somatic pain modulation processes involve the activation of A-beta primary sensory afferents that relate to the perception and suppression of pain. A-beta fibers are large, myelinated, fast sensory fibers. These fibers detect touch and vibration on the skin, muscles, and joints and act to reduce pain. Both nociceptive (A-delta) and non-nociceptive (A-beta fibers) converge at the substantia gelatinosa (part of the spinothalamic tract) within the dorsal horn of the spinal cord to code for the pain stimulus. When A-beta fibers are triggered, they suppress the nociceptive fibers via gamma amino-butyric acid (GABA) interneurons within the spinal cord that decrease the firing of nociceptors and thus decrease the brain's perception of pain.

Lymphedema is a state of protein-rich lymph and fluid accumulation due to stagnated or occluded lymphatic flow and/or venous insufficiency. Lymphedema is a common sequela of cancer, lymphadenectomy, burns, radiation therapy, injury, and infection. Congenital conditions that result in impaired lymphatic transport as is postulated to be in the case of Milroy's Disease also result in lymphedema. Patients with edema of the lower extremities sometimes experience a progressive situation in which the relatively higher intravascular hydrostatic pressure within the venous and arterial system results in fluid transference of plasma into the low-pressure extravascular space. The incompetent or diseased lymphatic system with its obstructed channeling system cannot accommodate the extra fluid and thereby results in distention of the skin and hypodermis. Soft tissue swelling typically occurs in the lower or upper extremities. At a critical point the skin may rupture, similar to an overinflated balloon. This may occur in single or multiple areas and result in numerous ulcerations that may take weeks, months, or years of medical care in order to heal. Long-term strategies for lymphedema management include compression and manual massage techniques, neither of which are completely efficacious. Furthermore, there is a significant personal disability and financial burden to the health care system that occurs as a result of payment for treatment and its associated comorbidities.

The wearable sleeves described in the present application may be used to enhance somatic pain modulation and lymphedema control, and may also alleviate other symptoms such as nausea, depression, insomnia, snoring, and pressure sores. Patients using these types of wearable sleeves may achieve a faster recovery from medical conditions, thereby both improving patient outcomes and reducing healthcare costs (e.g., with shorter hospital stays). Hospital patients undergoing surgery, and bed-confined patients that are at high risk of developing deep venous thrombosis may also benefit from the described wearable sleeves by minimizing the need for injectable anticoagulants postoperatively. Another use for these wearable sleeves is for a soldier, a hospital aid, or nurse, or a pregnant patient who would otherwise experience lower extremity swelling following an extended period of standing and/or walking. A wearable sleeve that is configured as a sock may decrease potential lower extremity and foot fatigue and edema. An individual who has sustained circumferential deep dermal burns of the hands or forearms may also benefit with a wearable sleeve configured as a glove or extended sleeve mitten. An individual who is diagnosed with Raynaud's phenomenon may also benefit due to the potential of improved blood flow changes in the hands or feet.

Figure 1:
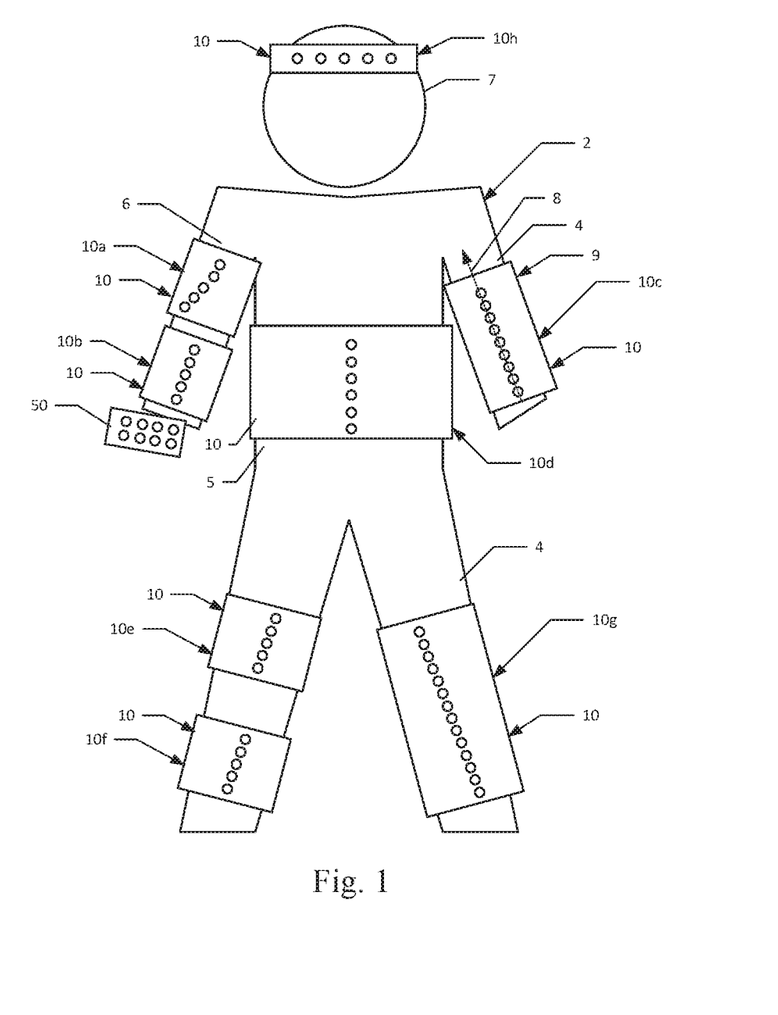
FIG. 1 is a front view of a plurality of wearable sleeves according to aspects of the disclosure, worn by a user.

Referring to FIG. 1, a device 9 is configured to be worn by a user 2, for example on a limb 4, a torso 5, or a head 7 of the user 2. According to one aspect of the disclosure, the device 9 can be in the form of a wearable sleeve 10 configured to be worn such that the wearable sleeve 10 contacts the user's skin 6. Alternatively, or in addition the wearable sleeve 10 can be configured to be worn over the user's clothes. During operation, the wearable sleeve 10 is configured to be disposed along a lymphatic drainage path 8 of the user 2.

As shown in the illustrated embodiment, the wearable sleeve 10 can be configured to be worn on a portion of the limb 4 of the user 2. According to one embodiment, the wearable sleeve 10 can be configured to be worn on a portion of an arm, for example an upper portion of the arm between the shoulder and the elbow of the arm. The wearable sleeve 10 can be configured such that a plurality of wearable sleeves 10 can be worn on the limb 4. For example a first wearable sleeve 10a is configured to be worn on an upper portion of an arm, and a second wearable sleeve 10b is configured to be worn on a lower portion of the arm, simultaneously. According to another aspect of the disclosure, the wearable sleeve 10 can be configured to be worn on multiple portions of the limb 4, the portions separated by a joint. For example, a third wearable sleeve 10c can be configured to be worn on both the upper portion and the lower portion of the arm, the upper and lower portions of the arm separated by an elbow.

Referring to FIGS. 2 to 5, the wearable sleeve 10 can include a sleeve body 12. The sleeve body 12 can be flexible, tubular, and elongate along an axis A. According to one aspect of the disclosure, the axis A is a central axis and the wearable sleeve 10 is configured to be worn such that during use, the axis A is approximately parallel to or coextensive with an axis along which the user's limb 4 is elongate. The wearable sleeve 10 can include a series of vibrating elements 14 attached to the sleeve body 12. According to one aspect of the disclosure, the wearable sleeve 10 is configured such that the vibrating elements 14 are disposed along a lymphatic drainage path 8 of the user. The vibrating elements 14 may each include a rotational source, such as a rotary motor with an eccentric rotating mass. Each of the vibrating elements 14 may be configured to provide stimulation to the limb 4 in the range of 1 to 20,000 Hz, for example, between 1 and 10,000 Hz or between 10,000 and 20,000 Hz. This range will ensure maximal user customizability in a safe, efficacious manner as the frequency is in the audible range and can be selected with relative ease either manually or via interaction through a cellular device application. Vibrational frequencies above 20,000 Hz are less likely to result in a distracting stimulus as they are in the inaudible ultrasonic range. Higher frequencies may also be associated with cellular cavitation as a side effect, which unless desired may result in irreversible destructive effects.

Figure 2:
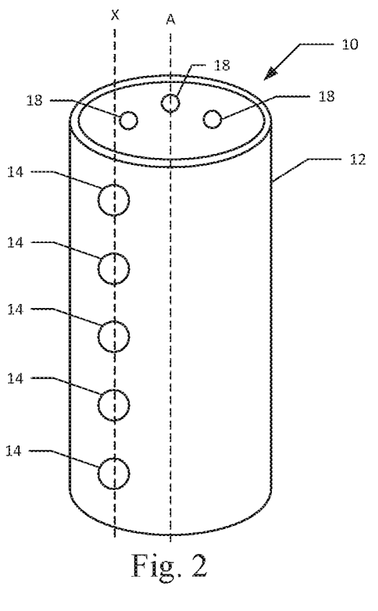
FIG. 2 is an isometric view of one of the wearable sleeves illustrated in FIG. 1, according to one embodiment.
Figure 3:
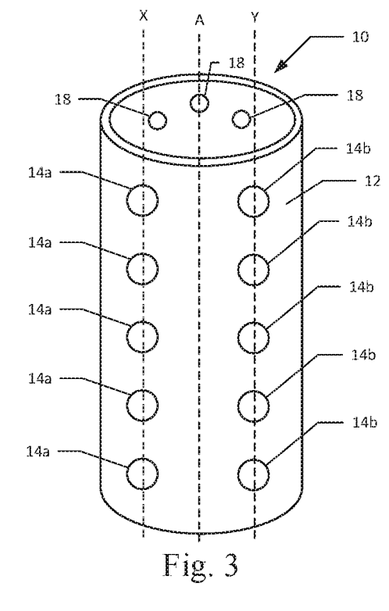
FIG. 3 is an isometric view of one of the wearable sleeves illustrated in FIG. 1, according to one embodiment.

Referring to FIG. 2, the wearable sleeve 10 can be configured such that the series of vibrating elements 14 are disposed along a line X that is parallel to the axis A. Referring to FIG. 3, the series of vibrating elements 14 can be a first series of vibrating elements 14a, and the wearable sleeve 10 can further include a second series of vibrating elements 14b that are disposed along a second line Y that is parallel to the axis A, and separated from line X. According to one aspect of the disclosure, the wearable sleeve 10 can be configured such that during use, lines X and Y are disposed along lymphatic drainage paths 8 of the user 2. According to one aspect of the disclosure, the wearable sleeve 10 can be configured such that during use, the line X extends along an anterior portion of the limb 4 and the line Y extends along a posterior portion of the limb 4.

Figure 4:
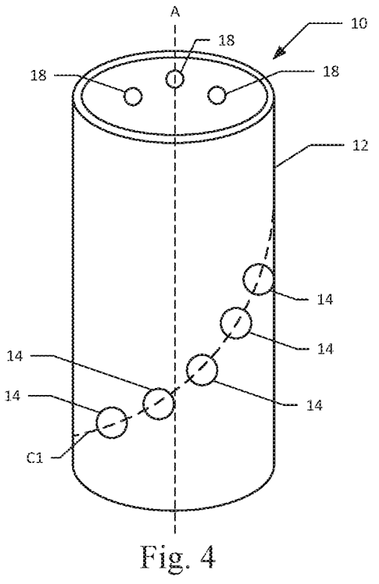
FIG. 4 is an isometric view of one of the wearable sleeves illustrated in FIG. 1, according to one embodiment.
Figure 5:
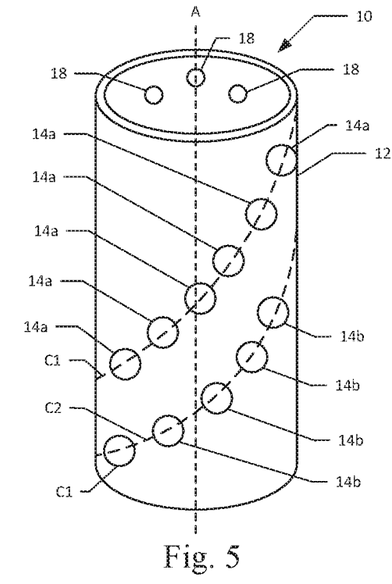
FIG. 5 is an isometric view of one of the wearable sleeves illustrated in FIG. 1, according to one embodiment.

Referring to FIG. 4, the wearable sleeve 10 can be configured such that the series of vibrating elements 14 are disposed along a curve C1 that extends about the axis A. Referring to FIG. 5, the series of vibrating elements 14 can be a first series of vibrating elements 14a and the wearable sleeve 10 can include a second series of vibrating elements 14b that are disposed along a second curve C2 that extends about the axis A. Curves C1 and C2 are shown in the illustrated embodiment as having different curvatures, but alternatively, C1 and C2 could have the same curvature. According to one embodiment, the wearable sleeve 10 is configured such that during use, at least one of the curves C1 and C2 are disposed along lymphatic drainage paths 8 of the user 2. In some embodiments, the wearable sleeve 10 may include multiple series of vibrating elements 14, some of which are disposed along straight lines, for example that are parallel to or perpendicular to axis A, and some of which are disposed along curves that are disposed about axis A.

Referring again to FIGS. 2 to 5, the wearable sleeve 10 may further include at least one light source, for example a light emitting diode (LED) 18, configured to expose a portion of the skin 6 on the limb 4 of the user 2 to light. For example, the LEDs 18 may be disposed circumferentially around axis A or in a spiral pattern about axis A. Exposure of the skin 6 to the LEDs 18 may reduce inflammation, improve muscle damage, promote fibroblast proliferation, wound healing, and rejuvenate skin. The LEDs 18 may be configured to target certain skin chromophores and thus stimulate endogenous endorphin sources. According to one embodiment, the LEDs 18 emit in a range between 400 nm to 700 nm. According to another embodiment, the LEDs 18 emit in a range between 500 nm to 1,300 nm. These ranges fall within an optical therapeutic window and will provide maximal photobiological mediated effects, which result in reduction in inflammation and pain when used in combination with at least one of the vibration and pneumatic elements.

Figure 6:
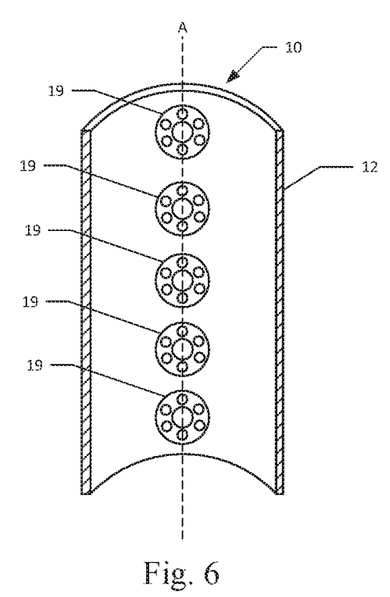
FIG. 6 is a cross-sectional view of one of the wearable sleeves illustrated in FIG. 1, according to one embodiment.
Figure 7:
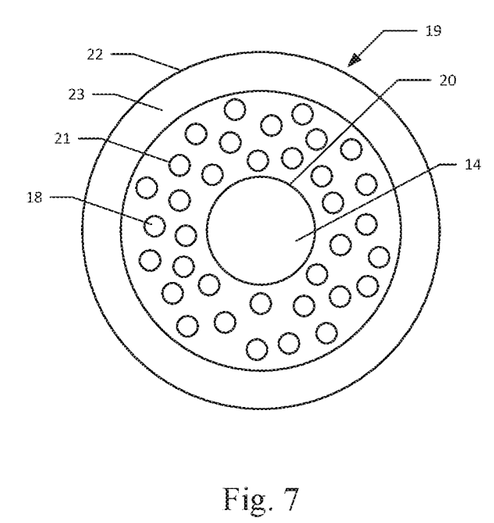
FIG. 7 is a top plan view of a disc of the wearable sleeve illustrated in FIG. 6.

Referring to FIGS. 6 and 7, according to one aspect of the disclosure the LEDs 18 can be situated on a plurality of base surfaces, for example a plurality of discs 19. Each disc may include a vibration source 20, a light source 21, a pressure source 22, or any combination thereof. For example, the vibration source 20 can include at least one of the series of vibrating elements 14, the light source 21 can include at least one of the LEDs 18, the pressure source 22 can include an inflatable portion 23, or any combination thereof. The light source 21 can include a plurality of different colored LEDs, for example red LEDs, yellow LEDS, orange LEDs, or any combination thereof. The plurality of different colored LEDs may be arranged in a pattern, or may be arranged randomly. The wearable sleeve 10 may include a pneumatic pump (not shown) configured to inflate the inflatable portion 23.

As shown in the illustrated embodiment, the base surface can be configured such that the vibration source 20 is positioned in the center of the disc 19, the light source 21 can be positioned around the vibration source 20 (radially outward from the vibration source 20 with respect to a center of the disc 19, and the pressure source 22 can be positioned around the light source 21 (radially outward from the light source 21 with respect to a center of the disc 19. The base surface may be positioned on the wearable sleeve 10 such that the base surface faces, for example directly touches the skin 6 during use of the wearable sleeve 10. The wearable sleeve 10 may further be configured such that wires and other components associated with the base surface may be disposed within layers of material of the wearable sleeve 10.

The wearable sleeve 10 may be configured such that the base surface, and portions thereof, may be configured to turn on/off in various patterns, for example in a sequence beginning at an extremity of the user 2 and progressing toward the user's heart, to reduce pain, lymphatic edema, and inflammation, as well as promote physiological healing and emotional relief. According to one aspect of the disclosure, the plurality of discs 19 can be sequentially arranged and sequentially triggered along the longitudinal axis A of the wearable sleeve 10, for example in order starting at the bottom and going up, or vice versa. Although the base surface is shown as being disc shaped, it will be understood that the base surface includes other shapes including non-circular ones.

Figure 8:
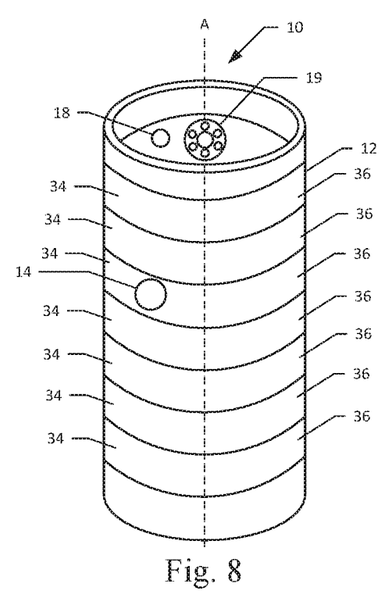
FIG. 8 is an isometric view of one of the wearable sleeves illustrated in FIG. 1, according to one embodiment.
Figure 9:
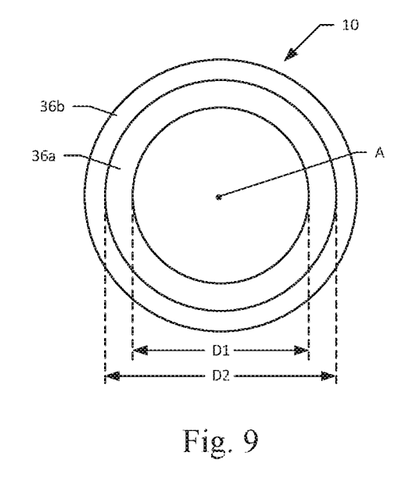
FIG. 9 is a top plan view of the wearable sleeve illustrated in FIG. 8.

Referring to FIGS. 8 and 9, the wearable sleeve 10 can include a series of compression elements 34, for example pneumatic compression elements, supported by the tubular sleeve body 12. The compression elements 34 may each include, for example, an inflatable ring 36 disposed about the axis A. Each of the inflatable ring 36 defines an inner diameter that fluctuates between an inflated configuration and a deflated configuration, the inflatable ring 36 transitioning from the inflated configuration to the deflated configuration through insertion and removal of air. As shown in the illustrated embodiment, a first of the inflatable rings 36a, in the inflated configuration defines a first inner diameter D1, which is less than a second inner diameter D2, which is defined by a second of the inflatable rings 36b in the deflated configuration.

The wearable sleeve 10 can be configured such that the first of the inflatable rings 36a and the second of the inflatable rings 36b have equal first inner diameters D1 when they are both in the inflated configuration, have equal second inner diameters D2 when they are both in the deflated configuration, or both. The wearable sleeve 10 can be configured such that the first of the inflatable rings 36a and the second of the inflatable rings 36b have different first inner diameters D1 when they are both in the inflated configuration, have different second inner diameters D2 when they are both in the deflated configuration, or both. The wearable sleeve 10, including the series of compression elements 34 can include at least one of the series of vibrating elements 14, at least one of the LEDs 18, at least one of the plurality of discs 19, or any combination thereof. Alternatively, the wearable sleeve 10, including the series of compression elements 34, can be devoid of any of the series of vibrating elements 14, any of the LEDs 18, and any of the plurality of discs 19.

Figure 10:
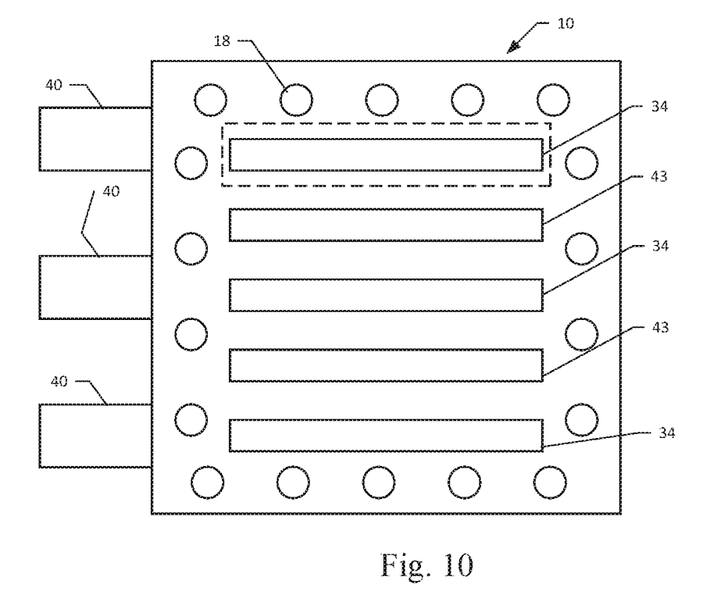
FIG. 10 is an isometric view of one of the wearable sleeves illustrated in FIG. 1, according to one embodiment, the wearable sleeve in a flat configuration.
Figures 11, 13:
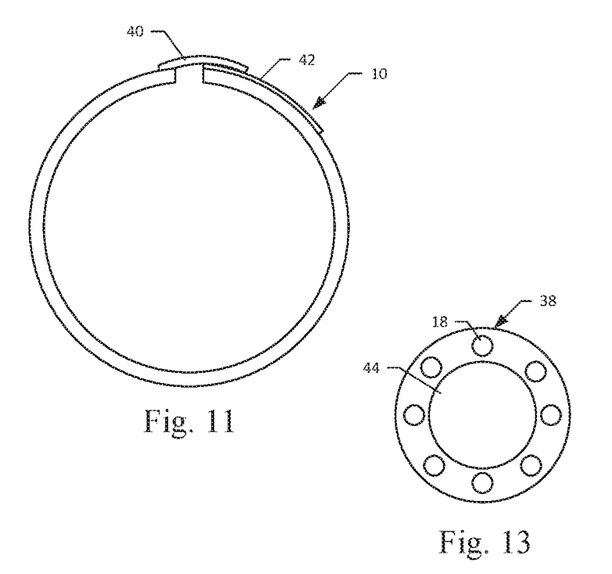
FIG. 11 illustrates the wearable sleeve illustrated in FIG. 10, the wearable sleeve in a first circular configuration.
FIG. 13 illustrates a top plan view of an inflatable disc of the wearable sleeve, according to one embodiment.
Figure 12:
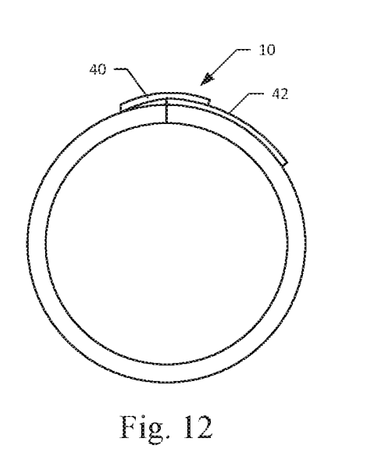
FIG. 12 illustrates the wearable sleeve illustrated in FIG. 10, the wearable sleeve in a second circular configuration.

Referring now to FIGS. 10 to 12, the wearable sleeve 10 may be configured to have a flat state (shown in FIG. 10) and a cylindrical state (shown in FIGS. 11 and 12) wherein the sleeve is wrapped around the limb 4 of the user 2. The wearable sleeve 10 may be configured to apply variable amounts of compression and size customization using, for example, hook and loop fasteners such as Velcro™. The wearable sleeve 10 can include one or more first portions 40 having one of the hooks or loops and one or more second portions 42 having the other of the hooks or loops. The wearable sleeve 10 can be configured such that the first portion 40 can be secured to the second portion 42 in a first location (as shown in FIG. 11) so as to define a first inner diameter D3 of the wearable sleeve 10, and the wearable sleeve 10 can further be configured such that the first portion 40 can be secured to the second portion 42 in a second location (as shown in FIG. 12) so as to define a second inner diameter D4 of the wearable sleeve 10 that is less than the first inner diameter D3. Thus, the wearable sleeve 10 can be configured to fit limbs of different sizes. Additionally, the wearable sleeve 10 can be configured to be secured to the limb 4 with different initial pressures, prior to inflation of the compression elements 34.

The wearable sleeve 10 can include at least one of the series of vibrating elements 14, at least one of the LEDs 18, at least one of the discs 19, at least one of the compression elements 34, or any combination thereof. As shown in the illustrated embodiment, the wearable sleeve 10 can include a series of the compression elements 34 and an outer perimeter of a plurality of the LEDs 18. As shown, the compression elements 34 can have a cylindrical shape when the wearable sleeve 10 is in the flat state and an annular shape when wrapped around the limb 4 of the user 2. Each of the compression elements 34 can be configured to transition from a deflated configuration (shown in solid lines) to an inflated configuration (shown in dashed lines) through insertion and removal of air.

The wearable sleeve 10 can include one or more electromagnetic strips 43. As shown in the illustrated embodiment, the electromagnetic strips 43 can be arranged between adjacent ones of the compression elements 34.

Referring to FIG. 13, alternatively to or in addition to the compression elements 34 having a cylindrical shape, the wearable sleeve 10 can include compression elements 34 shaped as inflatable discs 38. The inflatable disc 38, as shown in the illustrated embodiment, can include an inflatable bladder 44 and a plurality of LEDs 18 surrounding the inflatable bladder 44. Each of the inflatable discs 38 can define an inner diameter that fluctuates between an inflated configuration and a deflated configuration through insertion and removal of air during compression.

Like the vibrating elements 14, the compression elements 34 may be disposed within the wearable sleeve 10 so as to sequentially compress along a lymphatic drainage path 8 of the user. The wearable sleeve 10 may have an intermittent pneumatic compression component that inflates in regular intervals to improve blood circulation and lymphatic drainage. Specifically in relation to the disc 38, rather than encompassing the entire circumference of the user's body part, the disc 38 enables pneumatic compression to be targeted to and to occur along lymphatic channels to specifically relieve lymphatic obstruction. For example, a series of discs 38 may be disposed in patterns such as those described above in relation to the series of the vibrating elements 14.

Referring to FIGS. 1 to 13, in some aspects, the wearable sleeve 10 may be used to apply vibration from the vibrating elements 14 to activate A-beta sensory fibers which stimulate inhibitory neurons in the user's spinal cord that serve to suppress pain signals sent to the brain. The wearable sleeve 10 may include a control 50 that is configured to activate the vibrating elements 14 and the compression elements 34 to gently massage and apply pressure, respectively. The control 50 can be configured to provide a customizable pattern of vibration, compression, or both to relieve edematous body cavities and soft tissue. The control 50 can be wired to the sleeve body 12, or can be configured to communicate instructions to the sleeve body 12 wirelessly. The wearable sleeve 10 can be configured to adjust, for example by the remote 50, intensity of the vibration, light, pressure, or any combination thereof supplied by the wearable sleeve 10.

An embodiment of the wearable sleeve 10 can be configured to fit the torso 5 of the user 2 (see wearable sleeve 10d). The wearable sleeve 10d may include one or more of the compression elements 34 extending circumferentially along the torso 5, when the wearable sleeve 10d is worn on the torso 5, the compression elements 34 configured to inflate sequentially in a direction distal to proximal, or toward the heart. The wearable sleeve 10d may further be configured to inflate the compression elements 34 proximally to distally, or away from the heart, to facilitate digestive processes. In addition to lymphedema and pain relief, the compression effect on the torso 5 can relieve gastrointestinal symptoms relating to constipation, menstrual cramps, Irritable Bowel Syndrome, infection, and inflammatory bowel disease. One or more of the wearable sleeves 10, including the wearable sleeve 10d, may be used alone or in combination under clothing or applied onto the skin 6 with the user 2 in the laying, reclining, sitting positions, or the user 2 may be ambulatory.

The wearable sleeve 10 can be configured to fit an upper arm (see the wearable sleeve 10a). The wearable sleeve 10 can be configured to fit a lower arm, such as a forearm (see the wearable sleeve 10b). The wearable sleeve 10 can be configured to fit a whole arm (see the wearable sleeve 10c). The wearable sleeve 10 can be configured to fit a torso (see the wearable sleeve 10d). The wearable sleeve 10 can be configured to fit an upper leg (see the wearable sleeve 10e). The wearable sleeve 10 can be configured to fit a lower leg (see the wearable sleeve 10f). The wearable sleeve 10 can be configured to fit a whole leg (see the wearable sleeve 10g). The wearable sleeve 10 can be configured to fit a joint, such as but not limited to, an elbow, a shoulder, a wrist or a knee. The wearable sleeve 10 can be configured to fit at least a portion of a foot, for example such that the wearable sleeve 10 is configured as a sock. According to one embodiment, a kit is provided including a plurality of the wearable sleeves 10, for example at least a first of the wearable sleeves 10 configured to fit one body part, and a second of the wearable sleeves 10 configured to fit a different body part.

An embodiment of the wearable sleeve 10 can be configured to fit the head 7 of the user 2 (see wearable sleeve 10h). The wearable sleeve 10h can be configured to alleviate headaches. Thus, the wearable sleeve 10h can be configured for use by a user with little or no sensation below the neck. The wearable sleeve 10h can be configured as a headband, skull cap, helmet, or other structure configured to fit on the head 7 of the user 2.

The vibrating elements 14 and the compression elements 34 may be coordinated to rhythmically massage the lymphatic fluid in a specified, single direction or multiple directions. Each of the vibrating elements 14 and the compression elements 34 may be turned on or off manually, for example by the control 50, which may, for example, be held in the user's hand. In some embodiments, when the user turns on one of the vibrating elements 14 or one of the compression elements 34, one of the LEDs 18 associated with the vibrating element 14 or the compression element 34 that is otherwise deactivated can light up. The wearable sleeve 10 may include a plurality of the LEDs 18 such that they are configured to be activated in number to correspond in direct proportion to the intensity of the vibratory stimulation.

Figure 14:
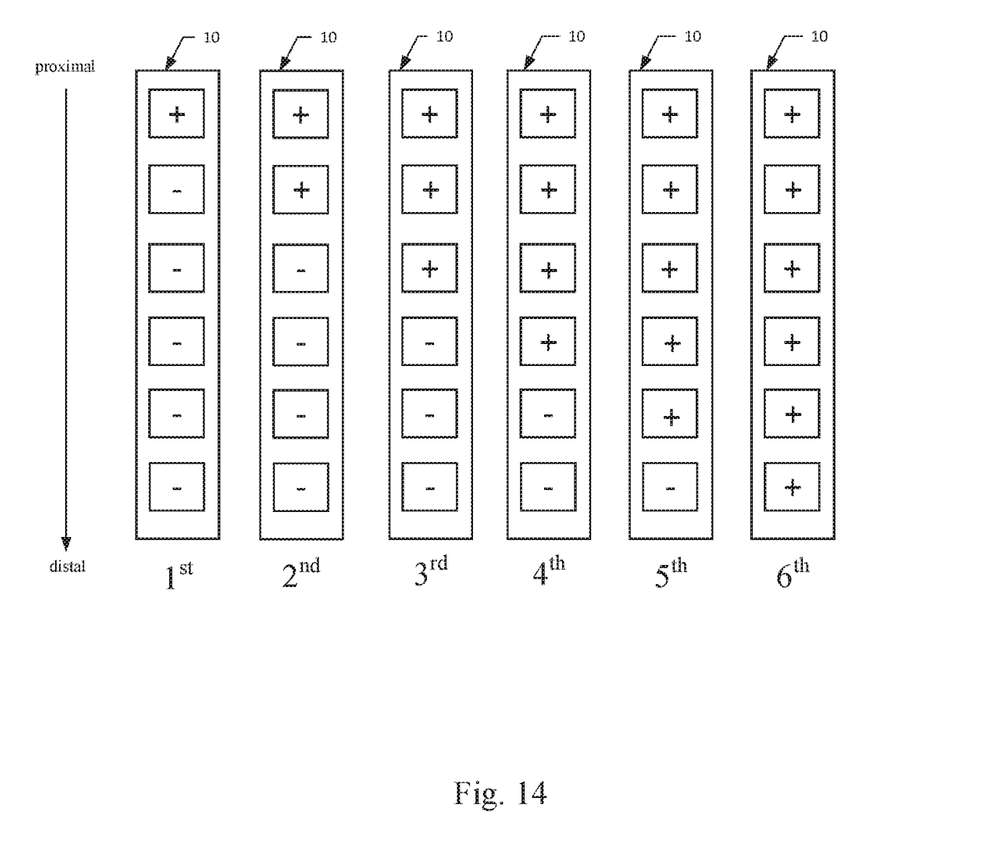
FIG. 14 illustrates a sample pattern by which vibrating elements, pneumatic elements, LEDs, or a combination thereof of the wearable sleeve may be activated.

Referring to FIG. 14, a schematic of the wearable sleeve 10 including the vibration elements 14, the compression elements 34, the LEDs 18, or any combination thereof. Each of the vibrating elements 14, the compression elements 34, and the LEDs 18 may be disposed anywhere in the depicted grid and separately controlled. The pattern of control may also be modified so that the user 2 does not get desensitized to a certain pattern of operation. For example, the frequency of vibration may be modified between treatment sessions. As shown, the wearable sleeve 10 can be activated sequentially such that the vibration elements 14, the compression elements 34, and the LEDs 18 in a proximal portion of the wearable sleeve 10 are activated first. Then the vibration elements 14, the compression elements 34, and the LEDs 18 in a second portion of the wearable sleeve 10 adjacent to and distal of the proximal portion are activated next. Then the vibration elements 14, the compression elements 34, and the LEDs 18 in a third portion of the wearable sleeve 10 adjacent to and distal of the second portion are activated next, and so on. The wearable sleeve 10 can be configured to be activated in the opposite order, distal to proximal, as well as in other non-sequential orders.

Referring again to FIGS. 1 to 13, the wearable sleeve 10, according to one aspect of the disclosure is configured to deliver a non-opioid pain control solution. According to one aspect of the disclosure, the wearable sleeve 10 may include a thermal, photonic, or radiofrequency-heating element that may be used to increase circulation by causing vasodilation in a vascularly compromised body part or limb. The heating element may be used as an applied array to a body part that needs more blood supply. The wearable sleeve 10 may also or alternatively have a hypothermal unit configured to cool the skin in the user 2 that already has vasodilation present so as to reduce hyperemia and inflammation. For example, the hypothermal unit may be used to treat a compartmental clinical situation such as shin splints. The wearable sleeve 10 may also or alternatively include vacuum suction to create distracting sensation. The wearable sleeve 10 may also or alternatively include a solar-based triggering mechanism such that vibration may be triggered to alert the user 2 that sunburn is imminent due to cumulative exposure.

According to one aspect of the disclosure, the wearable sleeve 10 can include an automated trigger mechanism configured to activate one or more of the functions of the wearable sleeve 10 without any direct input from the user 2. The automated trigger mechanism can include, for example, a timer. The timer can be configured to countdown to a pre-selected time, for example one hour from the time the pre-selected time is selected. Additionally, or alternatively the timer can be configured to countdown to a pre-selected time, for example 1:00 pm. Upon reaching the pre-selected time the automated trigger mechanism sends a signal to other components of the wearable sleeve 10, for example the vibrating elements 14, activating the vibrating elements 14, without any direct input from the user 2 at the pre-selected time. The wearable sleeve 10 may be configured such that the automated trigger mechanism can be activated by the control 50, for example the control 50 can include an input configured to input the pre-selected time.

The wearable sleeve 10 can include a motion sensor, and the wearable sleeve 10 can be configured to generate a stimulus (for example, auditory, tactile, both, etc.) detectable by the user. The stimulus can survive as a reminder to the user to move or change position, thereby decreasing the likelihood of developing bed sores or pressure sores. According to one aspect of the disclosure, the wearable sleeve 10 is configured such that if the motion sensor does not detect motion for about 120 minutes, the wearable sleeve 10 generates the stimulus. Upon detection of motion by the motion sensor, the wearable sleeve 10 ceases generation of the stimulus, resets the timer, or both. The automated trigger mechanism, the motion sensor, or both may allow paraplegic or quadriplegic users to benefit from the wearable sleeve 10.

According to one aspect of the disclosure, the wearable sleeve 10 can include a pain scale. The pain scale can include a range, for example from 1 to 10, and the pain scale may be configured such that the user 2 can select a value on the pain scale, for example a selected rating of "1" indicating the presence or anticipation of mild pain, and a selected rating of "10" indicating the presence or anticipation of severe pain. The wearable sleeve 10 can be configured such that the user 2 selecting a rating of "4" would effectuate the pain controlling mechanism(s) of the wearable sleeve 10 to be activated at approximately 40% of a maximum capacity.

During use, the wearable sleeve 10 may be configured to provide no direct muscle or nerve electrical stimulation to the user. In such embodiments, light, gentle vibration applied directly to the skin that may result in varying amounts of tapotement will be applied so as to activate cutaneous mechanoreceptors that indirectly trigger decreased pain signals relayed to the brain. This light vibration may also stimulate the movement of subcutaneous lymphatic fluid.

The wearable sleeve 10 may also include a sound triggering mechanism that may be activated to alert an individual who is snoring, suffering from sleep apnea, or other obstructive sleep disorder. The wearable sleeve 10 may be used alone or in conjunction with a source of auditory stimulus in order to treat insomnia. The wearable sleeve 10 may be worn and activated in order to alleviate symptoms of hyperemesis gravidarum, post-operative nausea, chemotherapy related nausea, or other forms of nausea. The vibrations and pneumatic elements will both distract the user from nausea and trigger pressure points on the skin that reduce nausea signals conveyed to the brain. Application of the wearable sleeve 10 to the Neiguan acupressure point in the forearm may promptly address nausea without the need for systemic medication.

The wearable sleeve 10 can be configured to apply optical radiation to the user 2 during the use. The optical radiation can be emitted at different wavelengths, at different intervals, and for different time durations. The wearable sleeve 10 can include a laser, which projects radiation having wavelengths in a concentric combination of infrared and visible laser light, for example between about 435 nm and about 1100 nm.

The duration, power, and wavelengths of the application of the laser can be configured primarily on a formulation of different factors, such as calf circumference, thigh circumference, abdominal circumference, hip circumference, patient weight, and patient height. For example, the wearable sleeve 10 can be configured to deliver to a patient having a thigh circumference of 38 cm, calf circumference of 31 cm, abdominal circumference of 76 cm, hip circumference of 82 cm, weight of 62 kg, ideal body weight of 50 kg according to Standard Metropolitan Life Insurance Company Tables, and height of 5 feet 3 inches, optical radiation for 7.0 minutes for each area of treatment. According to one embodiment, the time duration for exposure of each area on the skin 6 can be calculated based on the following expression: (Hip Circumference in cm)/(Abdominal Circumference in cm)×(Weight in kgs)/(Ideal Body Weight in kgs)×(Calf Circumference in cm+Thigh Circumference in cm)×Reduction Factor=Time in Minutes. Ideal Body Weight ("IBW") is as defined by Standard Metropolitan Life Insurance Company height-weight tables for IBW calculated from the patient's height. The Reduction Factor is 0.07 with a minimum exposure of 5.5 minutes per area. The maximum exposure per area for a majority of the patients is about 12 minutes. However, this number may vary depending on the above variables. Again, the power of the laser in the described embodiment is fixed. However, a laser having variable power settings can be employed, and the above relationship of variables adjusted for different power settings.

Exposure time per area being exposed can be between about seven and twelve minutes for an individual female or male adult of average build. For example, the thigh area can be treated in three sections, each area encompassing 120 degrees of the thigh with approximately 20% overlap. Thus, for each thigh, the total treatment time is approximately three times the duration of exposure for each area, or twenty-one to thirty-six minutes per limb. Alternatively, the wearable sleeve 10 can be applied and actuated in a circumferential fashion. The duration of exposure varies depending on the actual values of the above-mentioned variables. The laser can be administered as a continuous wave, or pulsating on the skin surface. The entire skin area to be treated may be covered by a single scan at a rate of 1 to 50 Hz.

Upon completion of the treatment session, a laser radiation emission or light emitting diode can then be administered to the skin surface at sixteen discrete sites along each single thigh. The sites are preferentially approximately the lymphatic drainage meridians known to those of ordinary skill in the art. Each site is exposed for a period of approximately 30 seconds. The sites correspond to different lymphatic drainage points, and are different for different parts of the body. Further, the optical radiation can be applied in a number of different patterns, such as oval, square, circle, etc., to most efficiently cover a target area as required. A more typical application involves a generally circular motion with or without compression and with or without vibratory stimulation, with an end vector directed into the general direction of the heart.

Although described primarily herein as being in the form of the wearable sleeve 10, the device 9 can also be a piece of fabric not in the form of a sleeve. For example, the device 9 can be attached, either separably or integrally to a piece of clothing. Additionally, the device 9 can be in the form of a hand held device, such as a wand.

Features of the disclosure that are described above in the context of separate embodiments may be provided in combination in a single embodiment. Conversely, various features of the disclosure that are described in the context of a single embodiment may also be provided separately or in any subcombination.

Changes could be made to the embodiments described above without departing from the broad inventive concept thereof. It is understood, therefore, that this disclosure is not limited to the particular embodiments disclosed, but it is intended to cover modifications within the spirit and scope of the present disclosure as defined by the claims.

What is claimed:

1. A wearable sleeve configured to be worn on a limb of a user, the wearable sleeve comprising:
   a tubular sleeve body, which is flexible and elongated along an axis; and
   a series of base surfaces secured to the tubular sleeve body such that each of the series of base surfaces is spaced from adjacent ones of the series of base surfaces along a direction parallel to the axis, each of the base surfaces sized so as to encompass less than an entire circumference of the tubular sleeve body;
   a series of vibration sources disposed on respective ones of the series of base surfaces and thereby attached to the tubular sleeve body, and
   a ring of LEDs configured to expose skin on the limb of the user to light, the ring of LEDs disposed on at least one of the series of base surfaces of the wearable sleeve that supports at least one of the series of vibration sources;
   wherein the series of base surfaces are secured to the tubular sleeve body at positions that align with a lymphatic drainage path in the limb of the user when the wearable sleeve is positioned on the limb.

2. The wearable sleeve of claim 1, further comprising a control which sequentially vibrates the series of vibration sources along the lymphatic drainage path of the user.

3. The wearable sleeve of claim 1, wherein the series of vibration sources are disposed along a line that is parallel to the axis.

4. The wearable sleeve of claim 3, wherein the series of vibration sources is a first series of vibration sources, and the line is a first line, the wearable sleeve further comprising a second series of vibration sources that are disposed along a second line that is parallel to the axis.

5. The wearable sleeve of claim 1, wherein the series of vibration sources are disposed along a curve that extends about the axis.

6. The wearable sleeve of claim 5, wherein the series of vibration sources is a first series of vibration sources, and the curve is a first curve, the wearable sleeve further comprising a second series of vibration sources that are disposed along a second curve that extends about the axis.

7. The wearable sleeve of claim 6, wherein the first curve has a curvature that is different from a curvature of the second curve.

8. The wearable sleeve of claim 1, wherein at least one of the series of vibration sources is configured to provide stimulation to the limb in a range of 1-20,000 Hz.

9. The wearable sleeve of claim 1 wherein the ring of LEDs are positioned radially outward from the at least one of the series of vibration sources with respect to a center of the at least one of the series of base surfaces.

10. A wearable sleeve configured to be worn on a limb of a user, the wearable sleeve comprising:
    a tubular sleeve body, that is flexible and elongated along an axis;
    a series of base surfaces secured to the tubular sleeve body such that each of the series of base surfaces is spaced from adjacent ones of the series of base surfaces along a direction parallel to the axis, each of the base surfaces sized so as to encompass less than an entire circumference of the tubular sleeve body; and
    a series of pressure sources disposed on respective ones of the series of base surfaces and thereby attached to the tubular sleeve body such that when the wearable sleeve is positioned on the limb the pressure sources are disposed along a lymphatic drainage path of the user;
    a control which sequentially compresses the compression elements along the lymphatic drainage path; and
    a ring of LEDs configured to expose skin on the limb of the user to light, the ring of LEDs disposed on at least one of the series of base surfaces of the wearable sleeve that supports at least one of the series of pressure sources.

11. The wearable sleeve of claim 10, wherein each of the series of pressure sources includes an inflatable disc that has a thickness that increases during compression so as to compress a portion of the limb of the user.

12. The wearable sleeve of claim 10, further comprising at least one vibration source.

13. The wearable sleeve of claim 10, wherein the series of pressure sources are pneumatic compression elements.

14. The wearable sleeve of claim 10 wherein the ring of LEDs are positioned radially inward from the at least one of the series of pressure sources with respect to a center of the at least one of the series of base surfaces.

15. A method of alleviating perceived pain of a user using a wearable sleeve disposed on a limb of the user, the method including:
- encircling at least a portion of the limb of the user with a tubular sleeve body of the wearable sleeve;
- positioning the wearable sleeve relative to the encircled limb of the user such that a series of base surfaces, each of which are spaced apart from adjacent ones of the series of base surfaces, align with a lymphatic drainage path in the encircled limb, wherein each of the series of base surfaces is sized so as to encompass less than an entire circumference of the tubular sleeve body; and the method including at least one of:
- activating a series of vibration sources attached to a tubular sleeve body of the wearable sleeve with a control of the wearable sleeve, wherein the series of vibration sources disposed on respective ones of the series of base surfaces such that the series of vibration sources are disposed along the lymphatic drainage path of the encircled limb of the user, and activating a ring of LEDs disposed on at least one of the series of base surfaces that supports at least one of the series of vibration sources thereby exposing skin on the limb of the user to light; or
- sequentially inflating a series of pneumatic pressure sources attached to the tubular sleeve body with the control of the wearable sleeve, wherein the series of pneumatic pressure sources are disposed on respective ones of the series of base surfaces such that the series of pneumatic pressure sources are disposed along the lymphatic drainage path so as to sequentially compress the encircled limb along the lymphatic drainage path of the user, and activating a ring of LEDs disposed on at least one of the series of base surfaces that supports at least one of the series of pneumatic pressure sources thereby exposing skin on the limb of the user to light.

16. The method of claim 15, further comprising both:
activating the series of vibration sources; and
sequentially compressing the series of pneumatic pressure sources.

* * * * *